(12) United States Patent
Hornebeck et al.

(10) Patent No.: US 9,115,212 B2
(45) Date of Patent: Aug. 25, 2015

(54) BIFUNCTIONAL PEPTIDE

(71) Applicants: REGENTIS INTERNATIONAL, Reims (FR); UNIVERSITE DE REIMS CHAMPAGNE ARDENNE, Reims (FR); CENTRE NATIONAL DE LA RECHERCHE SCIENTIFIQUE, Paris Cedex (FR)

(72) Inventors: William Hornebeck, Reims (FR); Joan Attia, Reims (FR); Sandrine Lorimier, Reims (FR); Frank Antonicelli, Witry-les-Reims (FR)

(73) Assignees: REGENTIS INTERNATIONAL, Reims (FR); UNIVERSITE DE REIMS CHAMPAGNE ARDENNE, Reims (FR); CENTRE NATIONAL DE LA RECHERCHE SCIENTIFIQUE, Paris Cedex (FR)

(*) Notice: Subject to any disclaimer, the term of this patent is extended or adjusted under 35 U.S.C. 154(b) by 0 days.

(21) Appl. No.: 14/375,414

(22) PCT Filed: Jan. 31, 2013

(86) PCT No.: PCT/FR2013/000033
§ 371 (c)(1),
(2) Date: Jul. 29, 2014

(87) PCT Pub. No.: WO2013/114013
PCT Pub. Date: Aug. 8, 2013

(65) Prior Publication Data
US 2015/0031633 A1 Jan. 29, 2015

(30) Foreign Application Priority Data

Feb. 1, 2012 (FR) ..................... 12 50932

(51) Int. Cl.
| | |
|---|---|
| *A61K 38/16* | (2006.01) |
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 14/81* | (2006.01) |
| *A61Q 19/08* | (2006.01) |
| *C07K 14/78* | (2006.01) |
| *C07K 5/083* | (2006.01) |
| *C07K 5/11* | (2006.01) |
| *A61K 8/64* | (2006.01) |

(52) U.S. Cl.
CPC ............... *C07K 14/8146* (2013.01); *A61K 8/64* (2013.01); *A61Q 19/08* (2013.01); *C07K 5/0804* (2013.01); *C07K 5/1019* (2013.01); *C07K 14/78* (2013.01); *A61K 38/00* (2013.01); *C07K 2319/00* (2013.01); *C07K 2319/50* (2013.01); *C07K 2319/75* (2013.01)

(58) Field of Classification Search
CPC ......... A61K 38/00; A61K 8/64; A61Q 19/08; C07K 14/78; C07K 14/8146; C07K 2319/00; C07K 2319/50; C07K 2319/75; C07K 5/0804; C07K 5/1019

See application file for complete search history.

(56) References Cited

FOREIGN PATENT DOCUMENTS

| | | |
|---|---|---|
| DE | 102004055541 A1 | 5/2006 |
| EP | 1275372 A1 | 1/2003 |
| WO | 03101376 A2 | 12/2003 |

OTHER PUBLICATIONS

Floquet et al. Structural Characterization of VGVAPG, an Elastin-Derived Peptide. Peptide Science, 2004. vol. 76, No. 3, pp. 266-280.*
Alix. A turning point in the knowledge of the structure-function-activity relations of elastin. J Soc Biol., 2001. vol. 195, No. 2, pp. 181-193, abstract only (3 pages).*
A. J. Alix, "A turning point in the knowledge of the structure-fuction-activity relations of elastin", Journal De La Societe De Biologie, Societe De Biologie, Paris, FR, vol. 195, No. 2, Jan. 1, 2001, pp. 181-193, XP009105680, ISSN:1295-0661.

* cited by examiner

*Primary Examiner* — Marcela M Cordero Garcia
(74) *Attorney, Agent, or Firm* — Andrew W. Chu; Craft Chu PLLC

(57) ABSTRACT

The bifunctional peptide is capable of activating collagen synthesis and inhibiting the production of matrix metallo-proteinases. The peptide has a sequence including three peptide parts A, B and C. The first peptide part A corresponds to a hexapeptide repeated at least three times, the part A being capable of bonding to a receptor elastin-binding protein in order to stimulate collagen synthesis. The second peptide part B corresponds to a tetrapeptide capable of acting as a competitive inhibitor of urokinase protease and of being cleaved by said protease. The third peptide part C corresponds to a tripeptide occupying at least one active site of the matrix metallo-proteinases in order to enable inhibition of the proteinases. The present invention further concerns a cosmetic and/or pharmaceutical composition incorporating the bifunctional peptide.

17 Claims, 10 Drawing Sheets

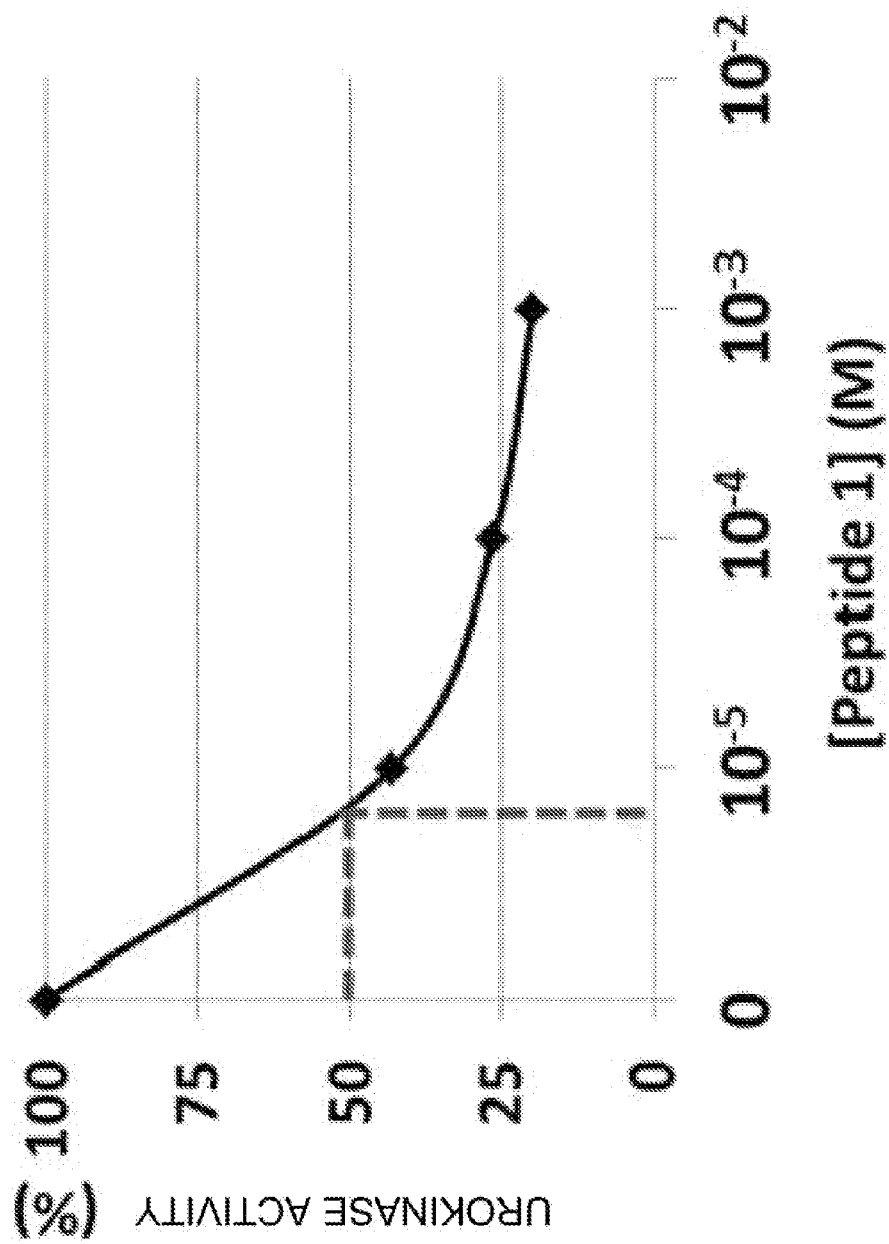

BIFUNCTIONAL PEPTIDE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to a peptide, which will find its application namely in the cosmetic and pharmaceutical fields.

The present invention will find its application mainly in the field of repair or regeneration of dermal tissue affected in particular by skin aging.

Skin aging is due to a more or less large imbalance of the synthesis control mechanisms and the degradation of the components of the extracellular matrix of the dermis, the latter constituting the innermost layer of the skin. Thus, during skin aging is observed in the extracellular matrix of the dermis, on the one hand, a decrease in the synthesis of certain macromolecules, namely collagen and elastin, and on the other hand, an increase in expression of certain enzymes such as the Matrix Metallo-Proteinases or MMPs. The latter namely exhibit a collagenolytic and elastolytic activity, and thereby contribute to the degradation of macromolecules of the matrix of the dermis. As a consequence, the dermis loses its tone, the skin distends, which results in the formation of wrinkles. This phenomenon can also be amplified by external factors, such as an exposure to ultraviolet rays, pollution, stress, or also tobacco.

2. Description of Related Art Including Information Disclosed Under 37 CFR 1.97 and 37 CFR 1.98

Traditionally, strategies are known from the prior art, which are aimed at slowing down the formation of wrinkles. Such strategies namely consist in:

- peeling or dermabrasion, which corresponds to an aggressive treatment of the skin in order to reduce the thickness thereof;
- the anti-wrinkle injections of hyaluronic acid or botulinum toxin, which have a wrinkle-filling effect and a targeted muscle paralysis temporarily reducing the wrinkles, respectively; these techniques are however expensive and show only short-term effects;
- the application of surface treatments, such as moisturizers, anti-wrinkle or smoothing creams, which slow down the formation of wrinkles, but without correcting those already formed;
- therapies based on autologous stem cells that are still poorly controlled.

Since a few years, other strategies are implemented by the laboratories in order to fight the effects of skin aging.

In particular, the use of chemical compounds such as N-acylaminoamide derivatives is provided in European patent application EP 1 275 372. More specifically, this document discloses a composition into which is incorporated, in addition to the above-mentioned N-acylaminoamide, a metalloproteinase inhibiting protein, the latter being involved in the degradation of collagen.

However, such a solution is not optimal, in particular because it requires, on the one hand, a combination of several compounds and, on the other hand, it does not permit to positively act on the synthesis of collagen.

The use of certain peptide derivatives has also been developed to prevent namely the symptoms of skin aging.

Therefore, for example from FR 285489 cosmetic compositions are known that include peptide derivatives, the latter proceeding from the elastin protein. More particularly, the peptide derivative may have the following sequence XXVGVAPGX (SEQ ID NO: 27), wherein the first X is R1, which corresponds to H or an alkyl chain comprising from 2 to 22 carbons, the second X is (AA) n, which corresponds to a peptide chain with AA consisting of any amino-acid or an amino-acid derivative and wherein n varies between 0 and 3, and the third X is R2, which corresponds to H or an alkyl chain comprising from 1 to 24 carbons.

A cosmetic composition incorporating such a peptide derivative permits namely a firming and restructuring effect.

However, such a peptide derivative or a composition incorporating this derivative does not permit to inhibit the activity and/or expression of MMP proteinases that are involved in the degradation of collagens, the latter constituting the major proteins of the extracellular matrix of the tissues of the body, and namely of the dermis. Collagen namely permits to confer to the tissues their resistance to tension forces. Thus, the peptide described in the above-mentioned document does not permit to prevent the degradation of this protein essential for preserving the skin tone.

From WO 2006053688 is also known a combination incorporating several peptides and used in anti-wrinkle treatment. In particular, these peptides of this combination are involved at several levels of the process of synthesis of collagen and/or fibronectin, namely by stimulating this synthesis.

DE 10 2004 055 541, in turn, discloses a composition including a combination of peptides in order to stimulate the release of the growth factor TGF-β, the latter being able to induce the synthesis of collagen.

However, the peptides described in these patent documents have the same drawbacks as those cited above, and namely the fact that the sequence proposed therein does not permit to reduce the expression of enzymes responsible for the degradation of the proteins of the extracellular matrix, and in particular of collagen.

SUMMARY OF THE INVENTION

The invention provides the possibility of coping with the various drawbacks of the prior art by providing a bifunctional peptide having both the property of stimulating the synthesis of collagens and that of inhibiting the proteinases involved in the cascade of degradation of the latter.

To this end, the present invention relates to a bifunctional peptide capable of activating the collagen synthesis and inhibiting the production of matrix metallo-proteinases, said peptide having a sequence including three peptide portions A, B and C, the first peptide portion A corresponding to a hexapeptide repeated at least three times, said portion A being capable of bonding to an elastin-binding receptor protein in order to stimulate the collagen synthesis, the second peptide portion B corresponding to a tetrapeptide capable of acting as a competitive inhibitor of the urokinase protease and of being cleaved by said protease, and the third peptide portion C corresponding to a tripeptide occupying at least one active site of the matrix metallo-proteinases in order to permit an inhibition of said proteinases.

Advantageously, the first peptide portion A stimulating the collagen synthesis has the XGXXPG (SEQ ID NO: 28) sequence, this sequence being repeated at least three times, with:

the first X corresponding to any amino acid,
the second X corresponding to an amino acid selected from Val, Thr, Gln, Ala, Leu, and
the third X corresponding to an amino acid selected from Ala, Leu, Ile.

More advantageously, the first peptide portion A of said peptide has the VGVAPG (SEQ. ID NO: 29) sequence.

Preferably, the second peptide portion B, cleavable by a protease, has the RXRX (SEQ. ID NO: 30) sequence, with the first X and the second X being Y1 and Y2, respectively, each corresponding to an amino acid selected from Ser, Tyr, Gly, Ala, Arg, Val, Leu.

More preferably, the second peptide portion B of said peptide has the RVRL (SEQ. ID NO. 31) sequence.

According to an interesting embodiment, the third portion C, permitting an inhibition of matrix metallo-proteinases, has the Z1-Ile-Z2 (XIX) sequence, with:

the first X being Z1 corresponding to an amino acid selected from Gly, Ile, Leu, and
the second X being Z2 corresponding to an amino acid selected from Leu, Phe, Ala, Ile, Val.

Even more advantageously, the third peptide portion C of said peptide has the Gly-Ile-Leu (GIL) sequence.

According to a preferred embodiment, the peptide according to the invention has the following sequence: VGVAPGVAVAPGVAVAPGRVRLGIL (SEQ. ID NO. 1), wherein the N-terminal and C-terminal ends correspond to N and OH, respectively.

However, the sequence of the bifunctional peptide according to the invention can also correspond to one of the sequences SEQ ID No. 2 to SEQ ID No. 26.

Preferably, the bifunctional peptide according to the invention is obtained by chemical synthesis. In addition, the peptide can advantageously be preserved in lyophilized form.

Advantageously, the bifunctional peptide according to the invention can be used for the treatment of chronic scarring diseases, namely the treatment of pressure sores or ulcers.

The bifunctional peptide according to the invention can also be used for the repair and/or regeneration of dermal tissue, namely for the treatment of skin aging.

The invention also relates to a cosmetic and/or pharmaceutical composition incorporating the bifunctional peptide according to the invention.

Preferably, the concentration of bifunctional peptide in the cosmetic composition is between 10 µg/mL and 1mg/mL, and preferably substantially equal to 100 µg/mL.

The bifunctional peptide according to the present invention has many advantages. On the one hand, it permits a stimulation of the synthesis of collagen proteins, namely of the type I and type III collagens. The increase in production of the latter type of collagen is particularly interesting; indeed, this type of collagen is referred to as "fetal" type collagen, because it is mainly synthesized in the fetal stage and during childhood. This type of collagen permits a particularly optimal healing of the tissues, referred to as "perfect" healing. On the other hand, said peptide permits to reduce collagenolysis by proteases. Furthermore, the stimulation of the collagen synthesis and the inhibition of the metallo-proteinases are obtained simultaneously thanks to the peptide portions A and C, respectively, of the bifunctional peptide, the latter including in addition a peptide portion B connecting the two other portions and being capable of being cleaved by urokinase. As a result, the peptide according to the invention can have a short sequence of about 25 amino acids, which facilitates its chemical synthesis.

Further features and advantages of the invention will become clear from the following detailed description of non-restrictive embodiment of the invention, with reference to the attached figures.

BRIEF DESCRIPTION OF THE DRAWINGS

FIGS. 6A and 6B are graph illustrations, showing the effect of the bifunctional peptide on the urokinase activity with respect to a synthetic substrate.

DETAILED DESCRIPTION OF THE DRAWINGS

Figure 1:
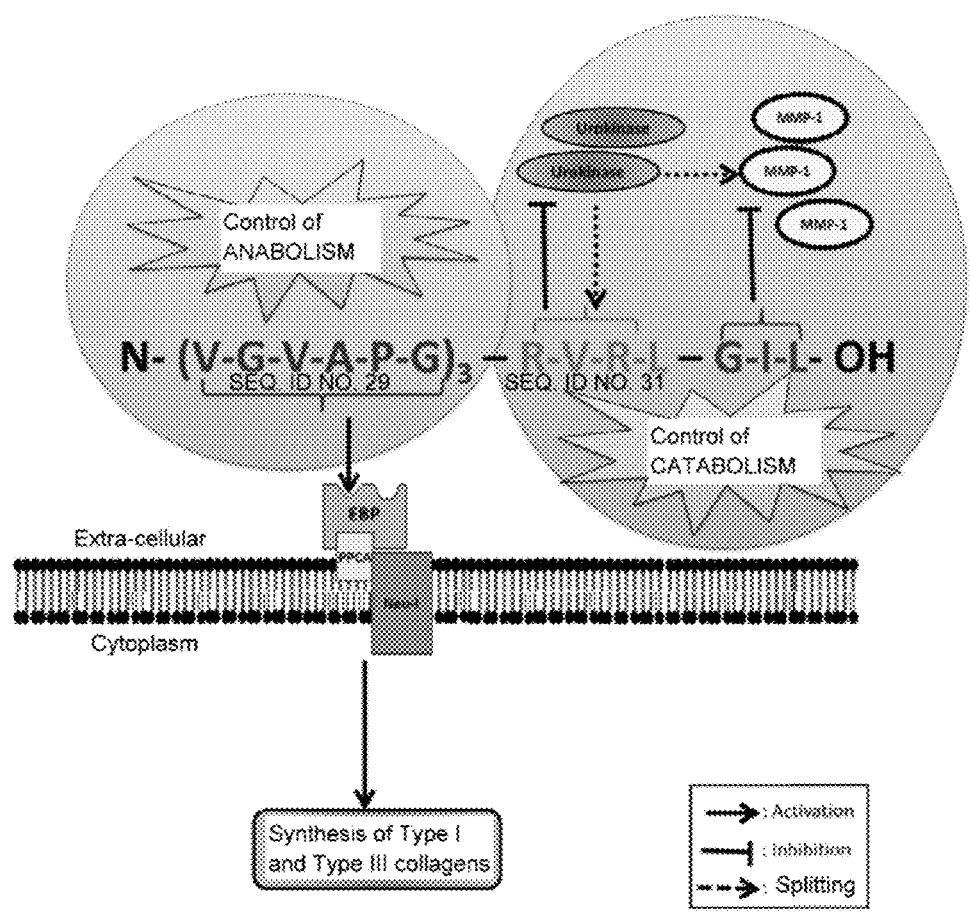
FIG. 1 is a schematic representation of the mechanism of action of the peptide according to the invention.

By way of a preliminary and informational indication, this specification uses the international three-letter code for designating the amino acids. Thus, Ala corresponds to alanine (A), Cys to cysteine (C), Asp to aspartic acid (D), Glu to glutamic acid (E), Phe to phenylalanine (F), Gly to glycine (G), His to histidine (H), Ile to isoleucine (I), Lys to lysine (K), Leu to leucine (L), Met to methionine (M), Asn to asparagine (N), Pro to proline (P), Gln to glutamine (Q), Arg to arginine (R), Ser to serine (S), Thr to threonine (T), Val to valine (V), Trp to tryptophan (W), and Tyr to tyrosine (Y).

Skin aging and the formation of wrinkles resulting from same are characterized, at cellular and molecular level, by a decrease in expression of the genes responsible for the synthesis of macromolecules entering into the composition of the extracellular matrix, such as collagens or elastin. In addition, the decrease in production of these matrix proteins is usually accompanied by an over-expression of enzymes, which are responsible for the degradation of the matrix proteins; these enzymes, the matrix metallo-proteinases or MMPs, are thus partly responsible for the decrease in tone at the level of the dermis, the distension of the skin and, in the end, the formation of wrinkles.

The collagen proteins are the predominant proteins in the constitution of the extracellular matrix of the body tissues. In particular, the collagens are present at about 90% at the level of the dermis, the latter constituting the solid support of the skin and playing both a nutrient and a temperature-control role, and a role of defense against pathogenic microorganisms. The dermis is mainly formed of so-called fibroblast cells, which take part in the synthesis, namely of collagen, as well as in the organization of the extracellular matrix.

Thus, the framing of the extracellular matrix is formed of collagen, but also of elastin, structural glycoproteins and proteoglycans. More particularly, the dermal matrix includes fibrils of type I and III collagen and a core of type V collagen.

The latter are likely to be degraded by so-called MMP proteins, the family of which includes not less than 26 members. More particularly, these proteins correspond to endopeptidases, i.e. which break the peptide bonds within the protein.

The studies conducted by scientists (Voorhes et al., Hornebeck et al., 2009) have permitted to demonstrate that the senescence of the skin cells, the fibroblasts, is characterized by an increased expression of these endopeptidases, namely as regards the MMP-1. The latter belongs to the group of the interstitial collagenases, and is responsible for the cleaving of the proteins of type I and III collagen. The MMP-1 is considered as being the main collagenase involved in skin aging, whether it is chronological or photoinduced.

Thus, the decrease of the dermal matrix proteins, and namely the collagens, associated with an increase of the degradation enzymes, namely the MMP-1, are important elements involved in skin aging, which results into a diminution of the skin tone and a formation of visible wrinkles.

Thus, in the framework of an inventive step the inventors have developed a peptide having multiple functions and permitting both to act at the level of the processes of synthesis of the collagen molecules as well as at different levels of the cascades of degradation of these very molecules.

And, in a particularly advantageous way, the bifunctional peptide according to the present invention has the peculiarity of promoting the restoring of a balance between the anabolic (synthesis) and catabolic (breakdown) processes of the extracellular, namely dermal, matrix.

In a particular preferable way, the peptide according to the invention is bifunctional and includes a sequence that can be divided into three portions:
- a first peptide portion, referred to as portion A, which advantageously has the capability of increasing the collagen synthesis;
- a second peptide portion, referred to as portion B, which preferably has a sequence recognized by a protease, the urokinase, whereby said peptide portion B can then be cleaved by this protease;
- a third peptide portion, referred to as portion C, the latter being capable of inhibiting the MMPs.

The peptide according to the present invention thus permits, on the one hand, to stimulate the collagen synthesis and, on the other hand, to reduce the degradation of said collagen by inhibiting the urokinase and the MMP proteases, namely the MMP-1.

More particularly, the peptide portion A, permitting an increase in collagen synthesis, consists of a hexapeptide, i.e. a succession of 6 amino-acid residues. Advantageously, this hexapeptide is repeated at least 3 times within the bifunctional peptide according to the present invention.

More preferably, the peptide portion A of the bifunctional peptide has the following sequence: XGXXPG (SEQ ID NO: 28). As stated above, this hexapeptide sequence, XGXXPG (SEQ ID NO: 28), is repeated at least three times within the peptide according to the invention. Indeed, some studies have shown that repeating three times said sequence provided different, even more interesting, results in terms of activity of the sequence (Alix 2001).

According to an interesting embodiment, the first X, second X, and third X, correspond to X1, X2, X3, wherein the X1 residue of the peptide portion A corresponds any of the amino acids. The residue X2, in turn, advantageously corresponds to an amino acid selected from Val, Thr, Gln, Ala and Leu. Finally, the X3 residue preferably corresponds to an amino acid selected from Ala, Leu and Ile.

Still more preferably, X1 and X2 correspond to Val and X3 corresponds to Ala. Thus, the hexapeptide corresponding to the portion A of the bifunctional peptide has preferably the sequence: VGVAPG (SEQ. ID NO: 29).

Such a sequence, repeated at least three times and associated with the peptide portions B and C, permit a significant stimulation of the protein expression of the collagens, namely as regards the type III collagen, as illustrated and explained in the attached FIGS. 3A and 3B and in example 1 below.

Figure 4:
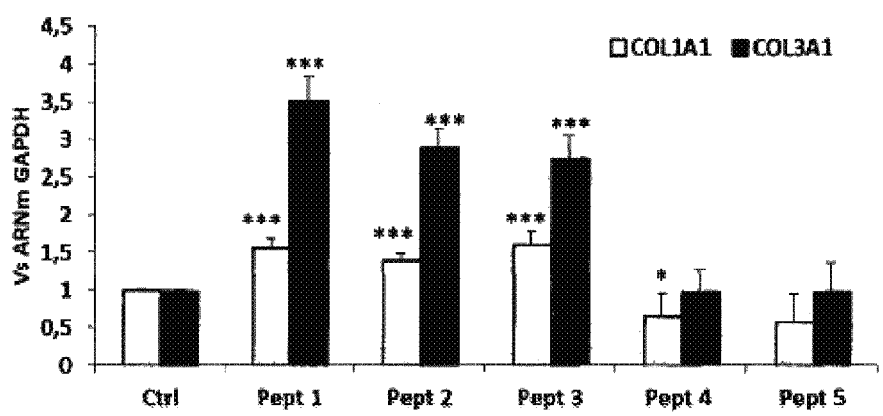
FIG. 4 shows a graph illustration in the form of a histogram of the gene expression of the COL1A1 and COL3A1 genes encoding respectively for type I and type III collagens in cultures of dermal fibroblasts treated with the peptide according to the invention or with fragments of the same peptide.

The peptide according to the invention also permits an increase of the gene expression of the COL1A1 and COL3A1 genes, as illustrated in FIG. 4, respectively encoding for type I collagen and type III collagen. The action of the bifunctional peptide on the synthesis of the type III collagen is particularly interesting; indeed, the latter is known as the majority collagen at fetal level and its production gradually decreases during childhood until it reaches a very low level of production in adults. By way of an example, type III collagen is 6 times less abundant in adults than type I collagen (Melissopoulos 1998; Herbage, 1997). The type III collagen is synthesized mainly by myofibroblasts during the healing, in order to replace the damaged tissues. At fetal level, type III collagen permits a so-called "perfect" healing (Lorena et al, 2002. Ferguson & O'Kane, 2004).

The sequence, VGVAPG (SEQ. ID NO: 29), of the bifunctional peptide according to the invention has been conceptualized from elastin peptides or élastokines resulting from the degradation of the elastic fibers. Such a sequence adopts a type VIII β-elbow shape, due to the presence of the proline and glycine residues within XGXXPG (SEQ ID NO: 28) (Floquet et al. 2004). This structural pattern is recognized by an elastin receptor protein, traditionally cited by its English name Elastin Binding Protein, and abbreviated as EBP. The latter is immobilized on the cell surface in association with two other subunits: a Protection Protein or Cathepsin A (PPCA) and a Neuraminidase (Neu-1), which are bonded to the cell membrane. The occupation of the EBP receptor protein by the peptide portion A of the bifunctional peptide, shown in FIG. 1, results into an activation of the molecular unit, which namely results into the synthesis of type I and type III collagen.

Such an activation of the molecular unit can also act on the chemotaxis, the proliferation, the adhesion and the survival of fibroblasts and also on the angiogenesis, the latter being essential in the process of revascularization of the chronic wounds, such as pressure sores or ulcers.

As regards the peptide portion B, it preferably consists of a tetrapeptide, i.e. a sequence including 4 amino acids.

More particularly, this tetrapeptide represents an arm that can interact, as a substrate or competitive inhibitor, with a serine protease, the urokinase. Thus, this permits to release the other two peptide portions A and C in the vicinity of the cell.

The Urokinase preferably cleaves a sequence having two Arg amino acid. Therefore, the peptide portion B advantageously has the sequence RXRX (SEQ. ID NO: 30), where the first X and second X correspond to Y1 and Y2, which correspond to amino acids.

According to a particular exemplary embodiment, Y1 and Y2 each correspond to an amino acid selected from Ser, Tyr, Gly, Ala, Arg, Leu and Val. These amino acids, associated with a cleavable Arg site, are preferably cleaved by the urokinase protease.

Even more preferably, the peptide portion B of the bifunctional peptide according to the invention includes the sequence RVRL (SEQ. ID NO. 31).

The urokinase protease is one of the activators of the plasminogen-plasmin system. The plasminogen is the physiological substrate of the urokinase, which will permit to activate it in the form of plasmin. This activation triggers a proteolytic cascade, which ends namely in activating the MMP-1 and MMP-3. The enzyme cascade of the plasminogen/plasmin system triggered by the urokinase protease is shown in the attached FIG. 2.

Thus, urokinase activity on the plasminogen is indirectly responsible for the degradation of the collagen, and namely the type I and type III collagen. Therefore, the presence of the peptide portion B in the bifunctional peptide according to the invention will act as a substrate or competitive inhibitor of urokinase. As a consequence, the latter will cleave the Arg sites present on the peptide portion B and will be less available to cause the inhibition of the plasminogen in plasmin; the degradation of the collagen molecules will thus be reduced. The effect of the peptide according to the invention on the activity of the urokinase is namely illustrated in FIGS. 6A and 6B.

As regards now the peptide portion C of the bifunctional peptide, it advantageously consists of a tripeptide, it is a sequence including 3 amino acids.

Preferably, the peptide portion C has the sequence Z1-Ile-Z2 (XIX), with the first X and the second X being Z1 and Z2, respectively, each corresponding to an amino-acid residue.

According to an interesting exemplary embodiment, Z1 is an amino acid selected from Gly, Leu and Ile, while Z2 is selected from Leu, Phe, Ala, Ile, Val.

Still more preferably, Z1 corresponds to Gly and Z2 corresponds to Leu. Thus, the peptide portion C of the bifunctional peptide advantageously has the sequence Gly-Ile-Leu (GIL). The tripeptide Gly-Ile-Leu (GIL) is indeed likely to occupy a portion of the active site of the MMP-1 and to act as a competitive inhibitor of the enzyme.

Indeed, these amino acids are of particular interest, because they are likely to have three of the pockets of the type I MMP, the P'1, P'2 and P'3 pockets. As a consequence, the active site of the type I collagenase can no longer chelate the Zn2+ ions, the latter being essential for the activity of said collagenase. The degradation of the collagen molecules by the MMP-1 is thus reduced thanks to the bifunctional peptide according to the invention. This is illustrated in particular in the attached FIGS. 7A and 7B.

Thus, according to a preferred embodiment, which permits to obtain interesting results in terms of collagen synthesis and inhibition of the MMPs, in particular of the MMP-1, the bifunctional peptide according to the present invention has the sequence: VGVAPGVAVAPGVAVAPGRVRLGIL (SEQ. ID NO. 1), wherein N-terminal and C-terminal ends correspond to N and OH, respectively.

Preferably, the sequence, VGVAPG (SEQ. ID NO: 29), is repeated 3 times; in other words, number of repeats, n, is preferably equal to 3. However, the sequence can also be repeated a number of times higher than 3.

The peptide according to the invention can also have, for example, the sequences identified as SEQ ID No. 2 to SEQ ID No. 26.

This list of sequences is however not exhaustive and thus not restrictive for the invention.

Namely, the amino acids of the sequences SEQ ID No. 1 to 26 can for example be substituted by amino acids that are chemically equivalent, i.e. having equivalent physical and chemical characteristics; substitutions between equivalent amino acids are performed for example between the non-polar aliphatic amino acids Ala, Val, Ile, Leu, or between the polar amino acids carrying a hydroxyl group Ser and Thr, among the amino acids Asn and Gln, between the amino acids carrying two acid functions Asp and Glu, etc. This information is listed in the database for proteases, the Merops (http://merops.sanger.ac.uk/).

The bifunctional peptide according to the present invention is preferably obtained by chemical synthesis.

Advantageously, the fluorenylmethoxycarbonyl technique (Fmoc)/tert-butyl (tBu) is implemented for obtaining the elongation of the peptide chains on Fmoc-Leu-Wang PS resins.

However, such an embodiment is not restrictive for the invention and the chemical synthesis of the bifunctional peptide can be obtained by any other suitable technique for this purpose and known to those skilled in the art.

Advantageously, the peptide according to the invention is lyophilized in order to ensure an optimum preservation thereof.

The bifunctional peptide according to the present invention is particularly interesting for use in the manufacture of cosmetic compositions aimed at promoting the repair and/or regeneration of dermal tissue. Indeed, through its action on the production of collagen, said peptide namely permits to limit the formation of wrinkles.

Figure 5:
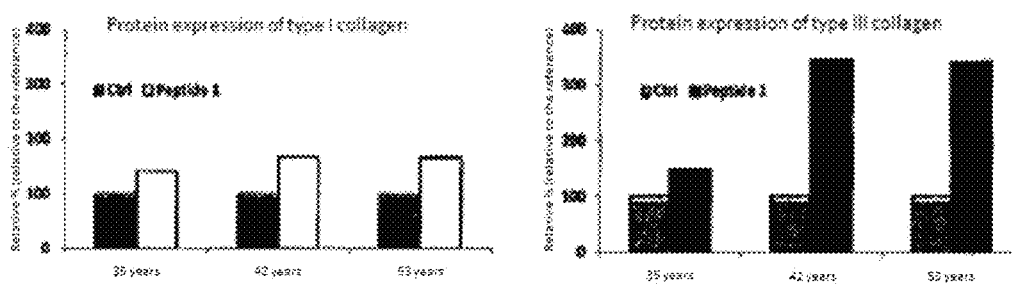
FIG. 5 shows graph illustrations, showing, depending on the age of the patients (35, 42 and 53 years old), the effect of the bifunctional peptide according to the invention on the protein expression of the type I and III collagens, respectively, from dermal fibroblasts from these patients.

In addition, it has been demonstrated by the inventors that the effect of the bifunctional peptide according to the invention on the production of collagen seemed to depend on the age of the patients. Indeed, the results shown in example 3 below, in connection with FIG. 5, show that the expression of type I collagen and especially the expression of type III collagen is greater in patients, who are older. Such results thus confirm the interest of said peptide for its use in cosmetic compositions for fighting skin aging.

However, such an embodiment is not restrictive for the invention. For example, the bifunctional peptide according to the invention can also be used for the preparation of pharmaceutical compositions.

Indeed, it turns out that a rupture of the balance between the synthesis of matrix proteins such as the collagen and the degradation of these same proteins can lead to the development of chronic wounds, also referred to as chronic scarring diseases, such as pressure sores, ulcers, or also severely burned persons. These diseases are in particular characterized by an over-expression of the matrix proteases MMPs and are generally associated with diseases such as diabetes or vascular diseases.

These chronic scarring diseases are steadily increasing in the developed countries, mainly because of the aging of the population. Therefore, the treatment and the management of these diseases represent a non-negligible cost.

At the cellular level, it has been shown that a large quantity of proteases, and namely MMP-1 type metallo-proteinases, was released in the vicinity of these chronic wounds of the pressure-sores type. Studies have also permitted to provide evidence that the activity of the type I collagenase, or MMP-1 increased significantly in the exudates of chronic wounds. Such an increase is responsible for the degradation of the molecules of type I and type III collagen, which are present in the vicinity of said wound (Barone et al, 1998. Shi et al, 2006.).

As regards now in particular the ulcers, it has also been demonstrated that large quantities of proteases were found in the vicinity of these wounds. In particular, studies have permitted to identify a rate of MMP-1 that is 65 times higher than normal, these MMPs then causing an excessive and prolonged degradation of the proteins of the extracellular matrix and also of the growth factors, leading to a delay in healing (Fischer et al. 2009).

Figure 2:
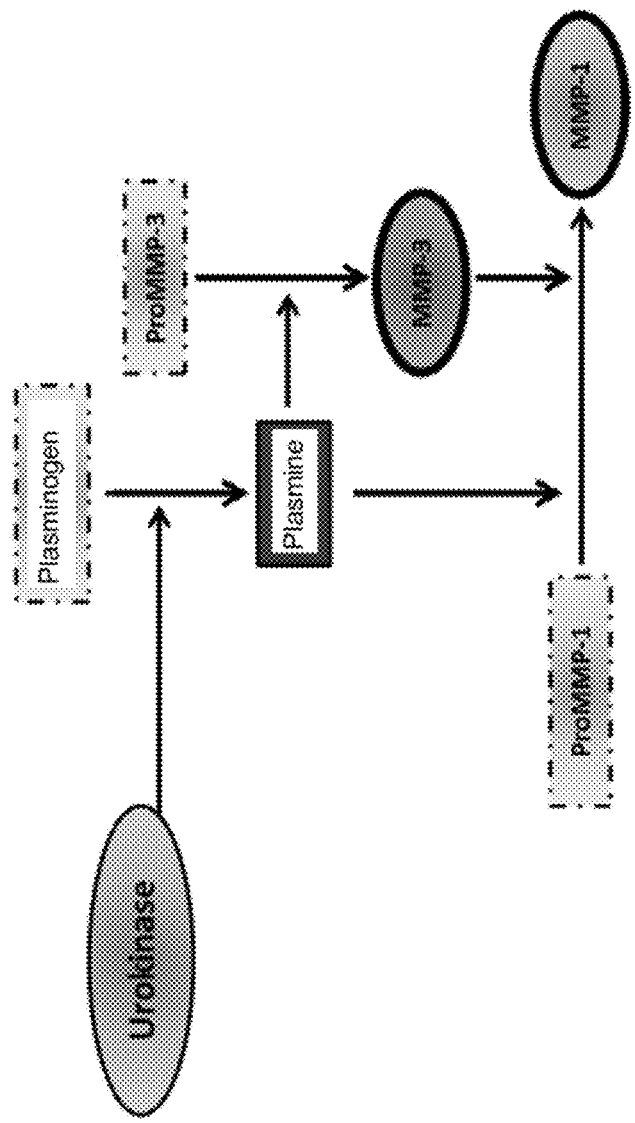
FIG. 2 is a schematic representation of the enzymatic cascade of the plasminogen/plasmin system.

Finally, it has been demonstrated that the concentration of urokinase activator of the plasminogen/plasmin system as visible in FIG. 2, and indirectly responsible for the activation of certain MMPs, was greatly increased namely in leg ulcers as well as at the level of the pressure sores (Werckroth et al. 2004).

Thus, it appears that the peptide according to the invention, which enables both a decrease of the activity of the MMP proteases and an increase of the synthesis of the matrix proteins, would contribute to facilitating the treatment of these chronic wounds and would replace the current medical treatments, which are heavy, expensive and inefficient.

According to a particular embodiment, the bifunctional peptide according to the invention is incorporated into a patch aimed at being affixed to the body region that is affected by a chronic wound.

However, such an embodiment is in no case limiting the invention, and it can easily be contemplated to incorporate the bifunctional peptide according to the invention in a preparation such as a cream, an ointment, a gel, etc., that can be applied on the wound to be treated.

According to an embodiment, the bifunctional peptide is used preferably at a concentration substantially between 10 μg/ml and 1 mg/ml. Indeed, no toxicity of the peptide according to the invention has been observed on dermal fibroblasts treated with peptide concentrations up to 1 mg/ml. In addition, studies conducted in order to find the toxicity genes through the SAM (Significance Analysis of Microarrays) statistical approach have shown that the cell death, the disruption of the conjunctive tissue and the tumor invasion are induced only from a high concentration of bifunctional peptide, higher than 1 mg/ml.

Still more preferably, the recommended concentration for use of the peptide, namely in the pharmaceutical and/or cosmetic compositions, is substantially equal to 100 μg/ml.

Further features and advantages of the invention will also become clear when reading the following examples, given by way of illustration and non-restrictively.

Example 1

Effect of the Bifunctional Peptide on the Collagen Synthesis—Protein Analysis

The dermal fibroblasts were isolated from abdomen skin biopsies obtained during surgery operations performed on healthy patients between 35 and 75 years of age.

After removing the epidermis, the fibroblasts were recovered by enzymatic digestion, then were cultured at 37° C. in DMEM (Dulbecco's Modified Eagle Medium) medium supplemented with 10% fetal calf serum and 1% penicillin/streptomycin.

The fibroblasts were then treated with the peptide having sequence VGVAPGVAVAPGVAVAPGRVRLGIL (SEQ. ID NO. 1), or various fragments of this sequence, at a concentration of 100 μg/ml. The various fragments tested are as follows:

peptide 1 (pept 1): peptide having the sequence VGVAPGVAVAPGVAVAPGRVRLGIL (SEQ. ID NO. 1), peptide 2 (pept 2): sequence VGVAPGVAVAPGVAVAPGRVRLGIL (SEQ. ID NO. 1), wherein N-terminal and C-terminal ends correspond to N and OH, respectively peptide 3 (pept 3): (VGVAPG (SEQ. ID NO: 29))3, wherein N-terminal and C-terminal ends correspond to N and OH, respectively peptide 4 (pept 4): RVRLIL (SEQ. ID NO. 32, wherein N-terminal and C-terminal ends correspond to N and OH, respectively peptide 5 (pept 5): N-Gly-Ile-Leu-OH The protein expression of the type I collagen and the type III collagen has then been shown by Western Blot and quantified by ImageJ. The results are shown respectively in the attached FIGS. 3A and 3B. The control (Ctrl) corresponds to the expression of type I and III collagen at the level of cells not treated with peptides. The experiments were performed in triplicate.

Figure 3A:
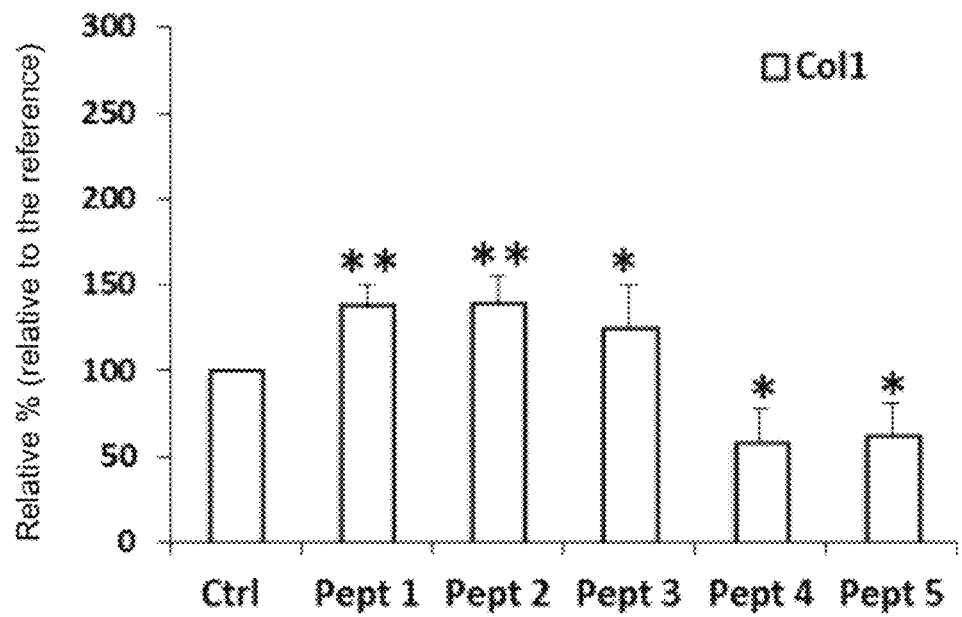
FIGS. 3A and 3B are graph illustrations corresponding to histograms illustrating the synthesis of type I and type III collagen, respectively, by fibroblasts treated with the peptide according to the invention at a concentration of 100 µg/ml or fragments of the same peptide.

The visible results in FIG. 3A show that the peptide according to the invention (pept 1) as well as the fragments (pept 2 and pept 3) incorporating the sequence, VGVAPG (SEQ. ID NO: 29), that corresponds to the portion A of the peptide according to the invention stimulate by 30% the protein expression of the type I collagen. The peptide fragments (pept 4 and pept 5) that do not include the portion A of the peptide according to the invention do not permit the stimulation of the synthesis of type I collagen; by contrast, the proportion of collagen synthesized when the fibroblasts are in contact with pept 4 and pept 5 seems to be smaller. The sequence, VGVAPG (SEQ. ID NO: 29), is therefore indeed responsible for stimulating the synthesis of type I collagen.

Figure 3B:
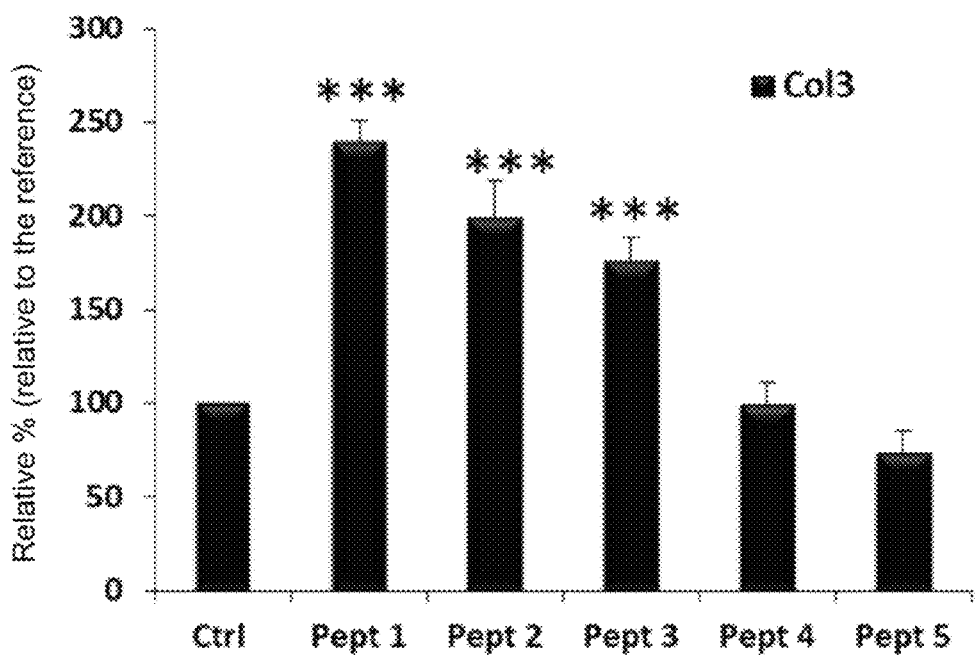

FIG. 3B shows that the peptide according to the invention having the sequence VGVAPGVAVAPGVAVAPGRVRLGIL (SEQ. ID NO. 1) permits to increase the synthesis of type III collagen; indeed, as can be seen in the histogram, the production of type III collagen is more than doubled when the fibroblasts are treated with the peptide having the sequence VGVAPGVAVAPGVAVAPGRVRLGIL (SEQ. ID NO. 1).

It is also interesting to note that a treatment of the fibroblasts with the peptide having the sequence VGVAPGVAVAPGVAVAPGRVRLGIL (SEQ. ID NO. 1) permits an increase in the synthesis of type III collagen by 36%, compared to the fibroblasts treated with the peptide having only the (VGVAPG (SEQ. ID NO: 29))3 sequence (pept 3). The other portions of the peptide according to the invention thus also play a role in the increase of the synthesis of type III collagen.

The peptide according to the invention is thus particularly interesting; indeed, in addition to permitting an increase of the synthesis of type I collagen, it also promotes the production of type III collagen.

Example 2

Effect of the Bifunctional Peptide on the Collagen Synthesis—Analysis of the Gene Expression The gene expression of the type I and III collagens in cultures of fibroblasts was also tested in the presence of the different peptides (pept 1 to pept 5) at a concentration of 100 µg/ml.

After 24 h of treatment with different peptides, the RNAs were extracted from the cultures using a RNeasy® kit (QIAGEN), then re-transcribed into complementary DNAs (cDNAs) using the RT2 First Strand Kit from SABiosciences™.

Real-time PCR analyses were then performed using the Mx3000p thermocycler from Stratagene in a 96-well plate. Each sample was analyzed in triplicate. The CDNAs serve as matrices in a reaction mixture containing the RT2 SYBR® Green/ROX™ qPCR Master Mix reagents (SABiosciences™) and the sense and antisense primers specific for the gene to be amplified. The reading of the fluorescence was performed at the end of each cycle and analyzed by means of the MxPro software (Stratagene). The relative expression of the COL1A1 and COL3A1 genes of interest coding for type I and type III collagen was obtained by normalizing the amount of products for amplifying the gene being studied by the amount of DNA amplified from a "domestic" gene, in this case the RNA of the gene encoding for the glyceraldehyde-3-phosphate dehydrogenase (GAPDH). As from the number of cycles corresponding to an amplification with a 100% efficiency, the relative quantity of cDNAs studied was calculated using the 2-AACT method (Livak & Schmittgen, 2001).

The results, visible in FIG. 4, confirm those obtained in the study of protein expression. The bifunctional peptide according to the invention as well as the peptide fragments pept 2 and pept 3 comprising the (VGVAPG (SEQ. ID NO: 29))3 sequence stimulate the gene expression of type I and III collagens. An increase of the synthesis of type III collagen was also observed when the fibroblasts were treated by means of the peptide having the sequence VGVAPGVAVAPGVAVAPGRVRLGIL (SEQ. ID NO. 1) with respect to the cells brought in the presence of the peptide 3 containing only the (VGVAPG (SEQ. ID NO: 29)) 3 sequence.

The derivative peptides pept 4 and pept 5 containing the Gly-Ile-Leu (GIL) sequence have no effect on the expression of the genes coding for type I and III collagens.

The control (Ctrl) corresponds to the expression of the genes coding for both types of collagen when the fibroblasts are not treated.

Example 3

Effect of the Bifunctional Peptide on the Collagen Synthesis—Tests of the Protein and Gene Expression Depending on the Age of the Patients Dermal fibroblasts from younger or older patients (35, 42 and 53 years old) were cultured and the bifunctional peptide according to the invention having the sequence VGVAPGVAVAPGVAVAPGRVRLGIL (SEQ. ID NO. 1) has been tested as to the protein and gene expression of type I and type III collagen. The results obtained as regards the protein expression of the two types of collagen are visible in FIG. 5. It appears that the action of the peptide according to the invention on the synthesis of collagen is greater when the fibroblasts proceed from older patients.

Example 4

Competitive Inhibition of the Urokinase by the Bifunctional Peptide

The action of the bifunctional peptide according to the invention on the urokinase, an enzyme upstream of the cascade of activation of the MMP-1 proteinase, was evaluated.

The activity of the urokinase on its synthetic substrate, D-Glu-Gly-Arg+NHPhNO2 L-Pyroglutamyl-glycyl-L-arginine-p-Nitroaniline hydrochloride (2444) has been tested in the presence and absence of the peptide according to the invention at different concentrations.

Figure 6A:
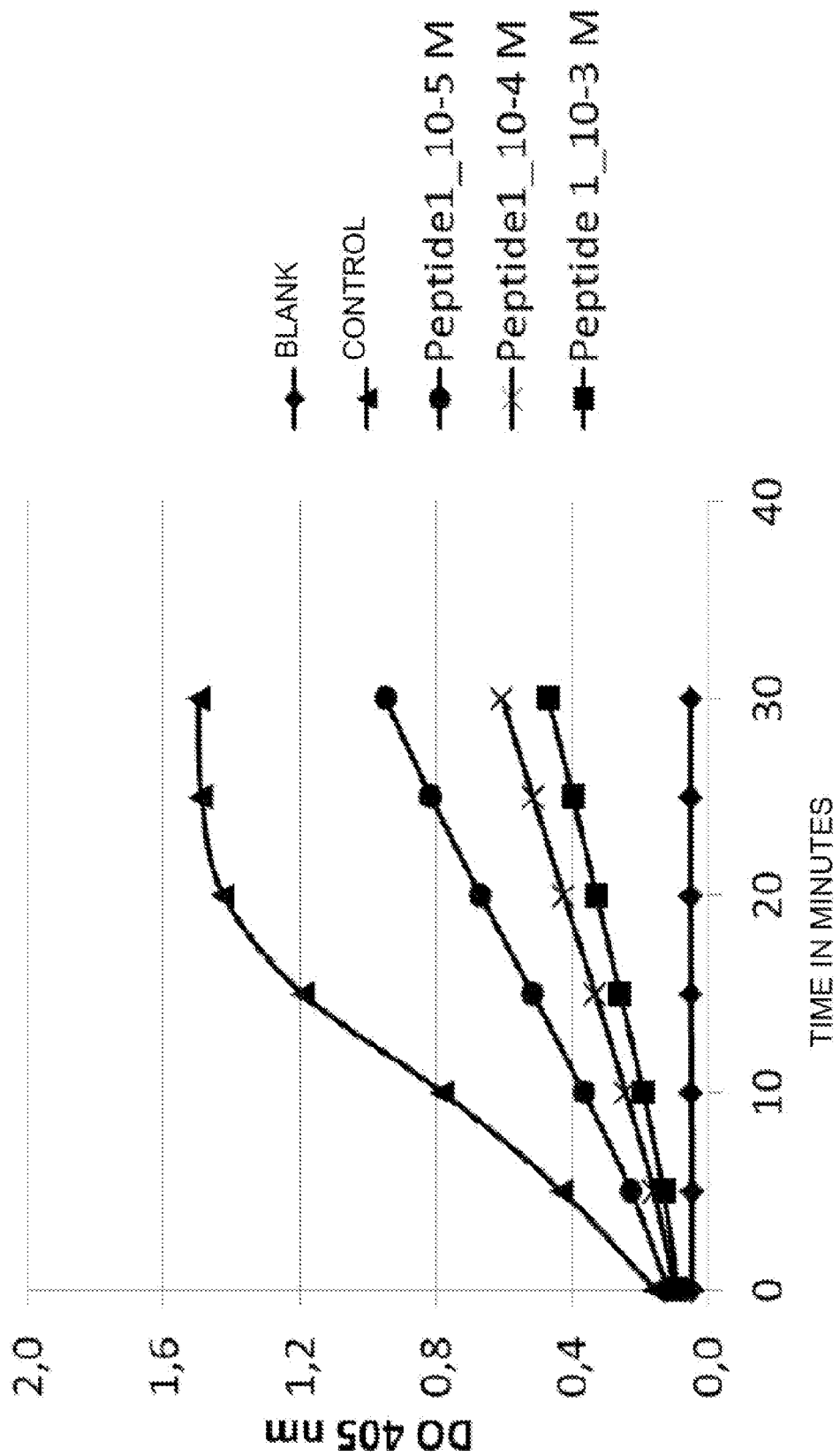

The results are shown in the attached FIGS. 6A and 6B.

A kinetics of hydrolysis of the substrate S2444 (0.3 nM) by the urokinase ($9.25*10^{-6}$ mM) was carried out in the presence of the bifunctional peptide having the sequence VGVAPGVAVAPGVAVAPGRVRLGIL (SEQ. ID NO. 1) and concentrated at $10^{-3}$, $10^{-4}$ and $10^{-5}$ M for 1 hour. The control corresponds to the kinetics in the absence of peptide. The enzyme activity was evaluated by measuring the absorbance (DO) at 405 nm every 5 minutes for a period of 35 min. The results are shown in FIG. 6A.

FIG. 6B is a graphical representation of the dose/effect relationship between the activity of the urokinase and the concentration of the bifunctional peptide used at time 15 min. The dotted line in the figure permits to determine the $IC_{50}$, i.e. the peptide concentration required to reduce the activity of the urokinase by 50%. The $IC_{50}$ corresponds to $0.83*10^{-5}$ M of peptide, i.e. a peptide mass concentration of 19 µg/ml.

It thus appears that the bifunctional peptide according to the invention behaves as a competitive inhibitor of urokinase.

Example 5

Effect of the Bifunctional Peptide on the Activity of the MMP-1 Protease

The effect of the bifunctional peptide according to the invention was then evaluated directly on the activity of the MMP-1, which is an enzyme downstream of the cascade activated by the urokinase.

The substrate of the MMP-1 that was used to test its activity in the presence of the peptide is a synthetic substrate, DNP-Pro-Cha-Gly-Cys (Me)-His-Ala-Lys (N-Me-Abz)-$NH_2$.

A concentration of 80 ng/µl of MMP-1 was brought in the presence of 0.4 ng/µl of synthetic substrate, in the presence or not of bifunctional peptide concentrated at $10^{-3}$, $10^{-4}$ and $10^{-5}$ M for 1 h. The results are shown in FIGS. 7A and 7B.

Figure 7A:
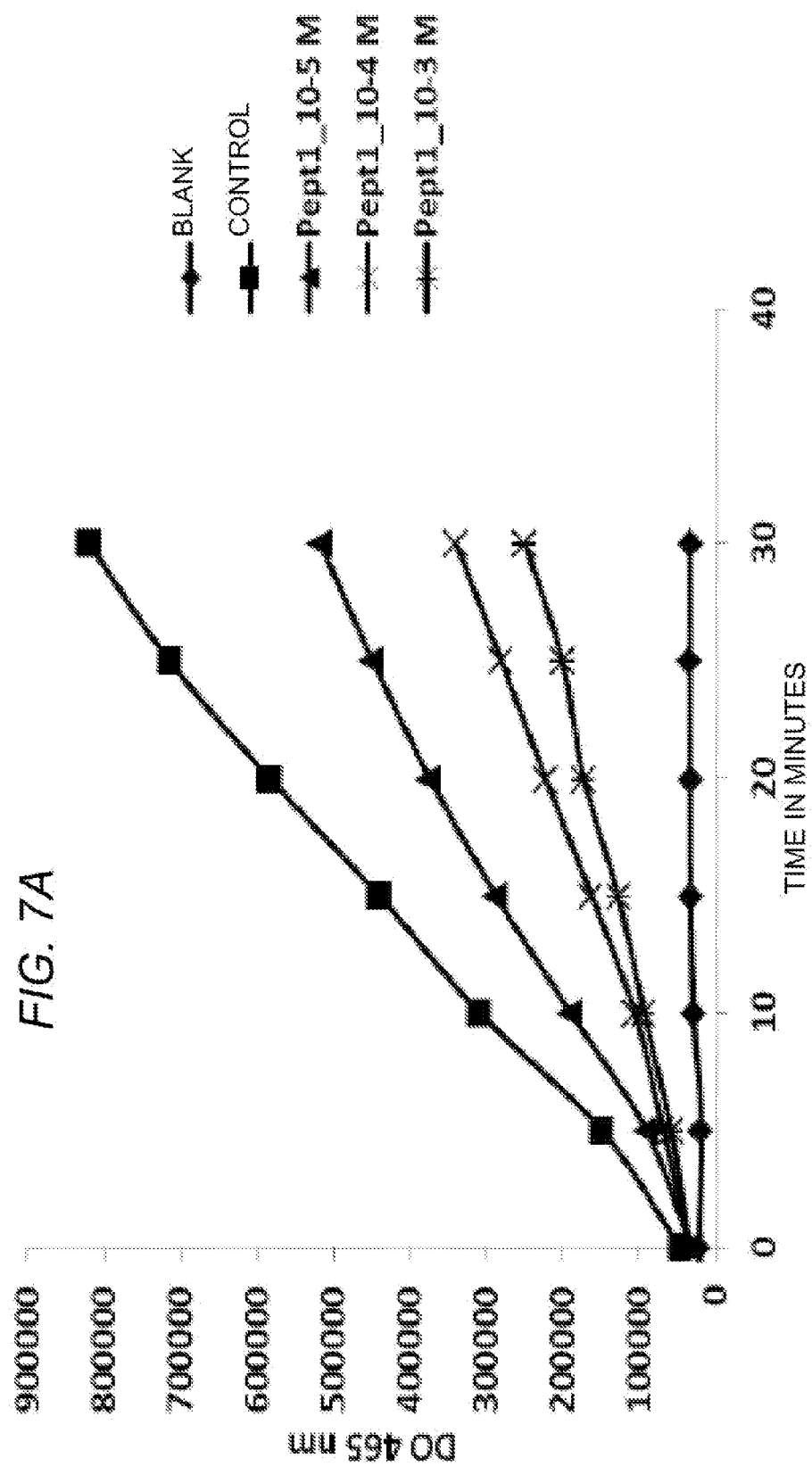
FIGS. 7A and 7B are graph illustrations, showing the effect of the bifunctional peptide on the activity of MMP-1 with respect to a synthetic substrate.

More particularly, FIG. 7A represents a kinetics of hydrolysis of the synthetic substrate of the MMP-1 in the presence or absence (control) of the peptide at different concentrations. The enzymatic activity of the MMP-1 was evaluated by measuring the absorbance (DO) at 465 nm every 5 minutes for a period of 35 min.

Figure 7B:
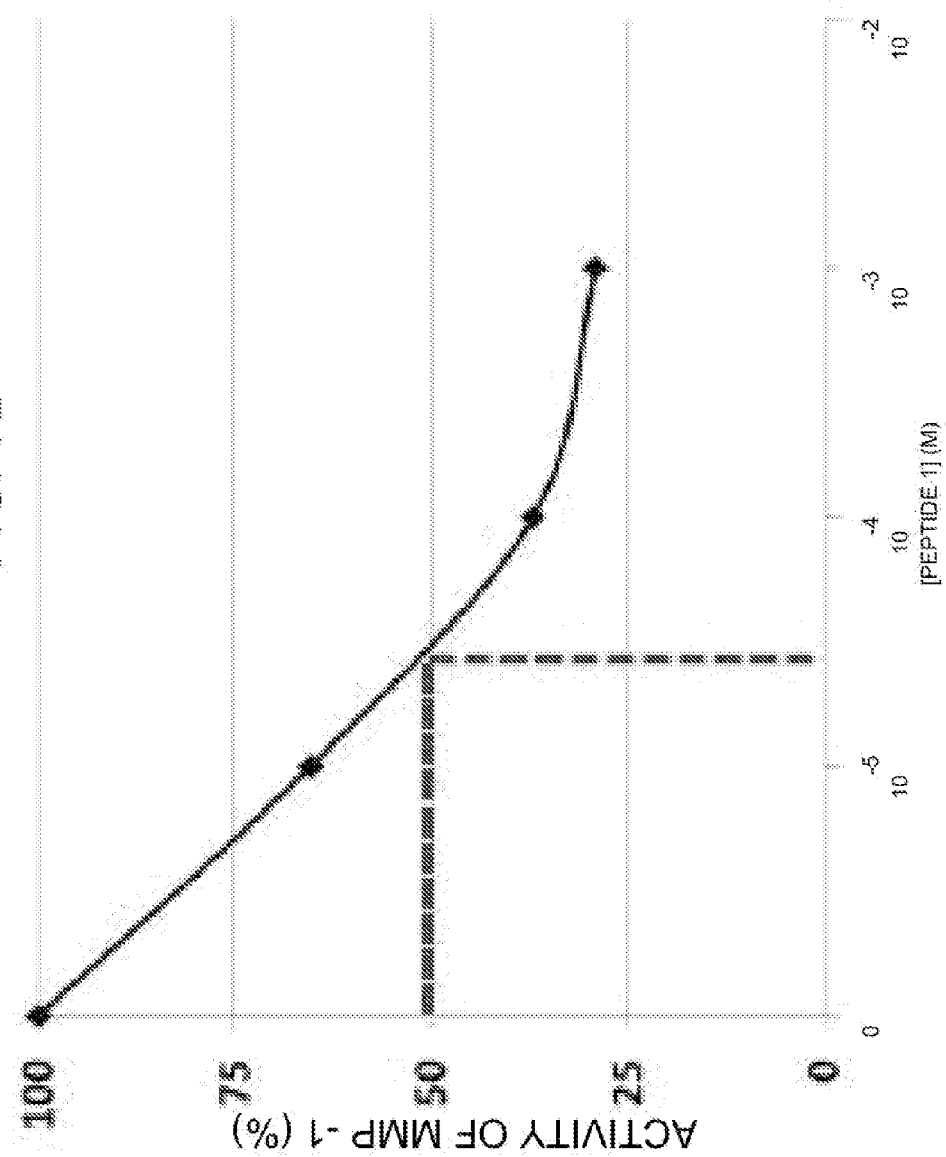

FIG. 7B is a graphical representation of the dose-effect relationship between the activity of the MMP-1 and the concentration of bifunctional peptide used at time 15 min. The dotted line in the figure permits to determine the $IC_{50}$, which here corresponds to $0.4*10^{-4}$ M, i.e. a concentration of bifunctional peptide equal to 91 µg/ml.

The effects of the peptide according to the invention were also tested on the activity of the MMP-1 in the presence of its natural substrate, i.e. the collagen fibers of human dermis.

To this end, the MMP-1 has previously been activated by APMA (4-aminophenylmercuric acetate) at 20 mM for 1 h30 at 37° C. The so activated MMP-1 was then deposited on cuts of skin having a thickness of 5µ in the presence or absence of the peptide according to the invention (100 µg/ml). After 3 h, the cuts of skin were immunostained, in order to reveal the presence of type I and III collagen, then observed by confocal microscopy. The results, not shown, show that, at the level of the cut that has not been treated with the peptide, the collagens I and III were fully degraded by the MMP-1. On the other hand, in the presence of the bifunctional peptide, the action of said MMP-1 was inhibited; indeed, the collagens I and III were detected.

The bifunctional peptide according to the invention inhibits the degradation of the collagens by inhibiting in situ the activity of the MMP-1.

Example 6

Cleavage of the Bifunctional Peptide by the Urokinase

At the pericellular level, an excess of urokinase was observed, of about $10^{-4}$ M. The peptide could thus be cleaved by the urokinase, the latter acting in particular at the level of the arginine residues (Arg) of the portion B of the peptide according to the invention.

Figure 8A:
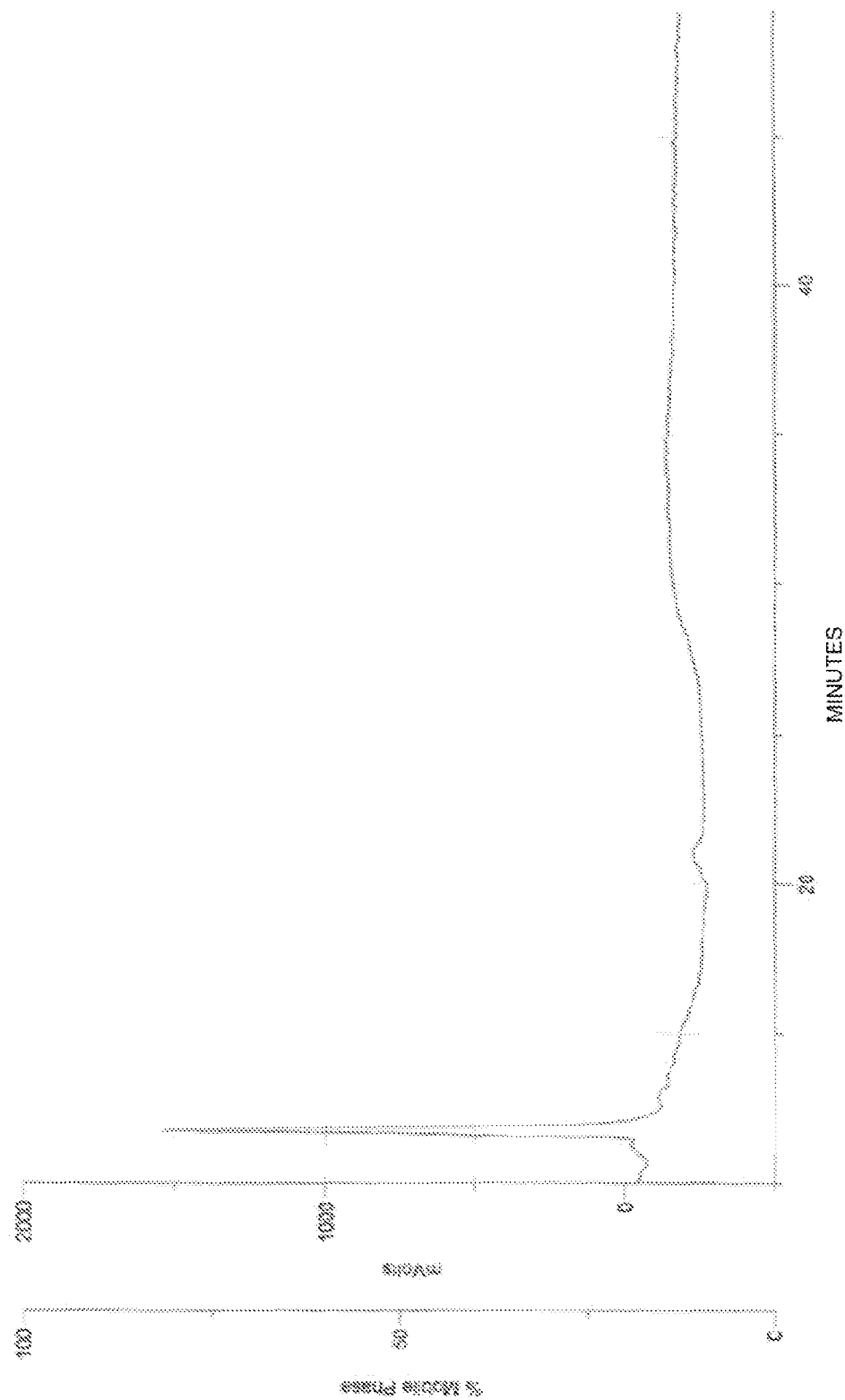
FIGS. 8A and 8B are graph illustrations, showing the elution profile of the peptide according to the invention, respectively without treatment and with treatment with urokinase.
Figure 8B:
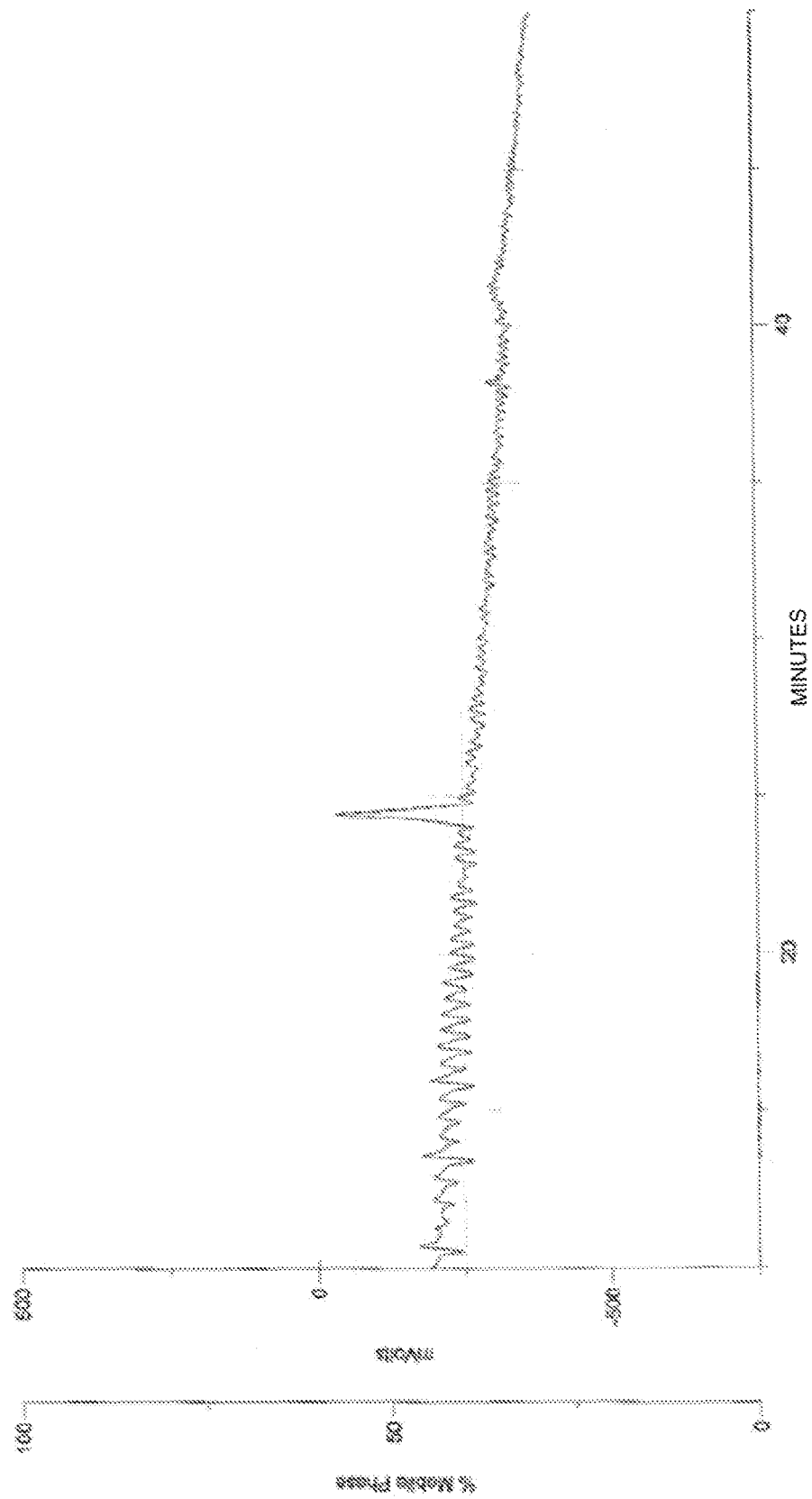

Studies were conducted by HPLC on a Chromolith Jupiter C18 column (50×4.6 mm), and applying a linear gradient of 0.1% TFA of acetonitrile in 0.1% TFA of water, 0 to 100% for 100 min. The results showed the presence of a spectral peak at 11.75 min, which is characteristic for the bi-functional peptide (FIG. 8A). However, after the action of an excess of urokinase on the bifunctional peptide (0.45 mM), the spectral peak was different; indeed, the new peak was eluted at 20 min, thus characterizing a cleavage of the bifunctional peptide by the urokinase (FIG. 8B).

Thus, under conditions of skin aging, in presence of large quantities of urokinase, the bifunctional peptide according to the invention is cleaved, thus releasing the C-terminal of said peptide incorporating the Gly-Ile-Leu (GIL) sequence.

Example 7

Effects of the Gly-Ile-Leu (GIL) Sequence on the Activity of the MMP-1

The Gly-Ile-Leu (GIL) sequence was selected by the inventors for its capability of occupying the P'1, P'2 and P'3 pockets of type I collagenase, the MMP-1. The activity of the latter has been tested on the synthetic substrate, the DNP-Pro-Cha-Gly-Cys (Me)-His-Ala-Lys(N-Me-Abz)-NH$_2$, in the presence or absence of the peptide 5 having the Gly-Ile-Leu (GIL) sequence at concentrations of $10^{-5}$, $10^{-4}$ and $10^{-3}$ M.

The results (not shown) demonstrate that the peptide 5 decreases in a dose-dependent way the activity of the MMP-1 on its synthetic substrate. The IC$_{50}$ of the Gly-Ile-Leu (GIL) peptide was measured; it was $0.71*10^{-4}$ M, i.e. a peptide concentration of 21.3 µg/ml.

The terminal portion C, GIL (SEQ. ID NO. 33), of the bifunctional peptide according to the invention can thus be generated in the event of an excess of urokinase and cause an inhibition of the activity of the MMP-1. These data confirm the importance of the peptide for fighting skin aging and/or for the healing of chronic wounds.

Studies were also conducted on a model of more comprehensive study: the ex vivo skin models permit to mimic skin aging and some associated pathologies. The results obtained are not shown, but they confirm the results obtained in vitro.

Of course, the invention is not limited to the examples shown and described above, which may have variations and modifications without departing from the scope of the invention.

BIBLIOGRAPHY

Alix, A. J. A turning point in the knowledge of the structure-function-activity relations of elastin. J Soc Biol 2001; 195 (2):181-93

Barone, E. J., et al., Interleukin-1alpha and collagenase activity are elevated in chronic wounds. Plast Reconstr. Surg, 1998 102(4): p. 1023-7; discussion 1028-9.

Ferguson, M. W. and S. O'Kane, Scar-free healing: from embryonic mechanisms to adult therapeutic intervention. Philos Trans R Soc Lond B Biol Sci, 2004 359(1445): p. 839-50.

Fisher, G. J., et al., Collagen fragmentation promotes oxidative stress and elevates matrix metalloproteinase-1 in fibroblasts in aged human skin. Am J Pathol, 2009 174 (1): p. 101-14.

Floquet, N., Héry-Huynh, S., Dauchez, M., Derreumaux, P., Tamburro, A. M., Alix, A. J. Structural characterization of VGVAPG, an elastin-derivëd peptide. Biopolymers, 2004; 76 (3):266-80. Review Herbage, D. Collagènes et protéoglycannes du derme: données actuelles, in Biologie de la peau. 1997

Hornebeck, W., Inflamm-âge et cascades protéolytiques. Médecine et longévité. Vol. 1. 2009: Elsevier Masson. 38-43

Livak, K. J. and T. D. Schmittgen, Analysis of relative gene expression data using real-time quantitative PCR and the 2(-Delta Delta C(T)) Method. Methods, 2001 25(4): p. 402-8.

Lorena, D., et al., Normal scarring: importance of myofibroblasts. Wound Repair Regen, 2002 10(2): p. 86-92.

Mélissopoulos A., L. C., La peau. Médicales et internationales ed. 1998.

Shi, B., et al., Effect of vacuum assisted closure on collagenase activity in human chronic wound. Zhonghua Zheng Xing Wai Ke Za Zhi, 2006 22(6): p. 465-7.

Voorhees, J. J., et al, Collagen degradation in aged/photodamaged skin in vivo and after exposure to matrix metalloproteinase-1 in vitro. J Invest Dermatol, 2003; 120(5): p. 842-8

Weckroth, M., et al., Epithelial tissue-type plasminogen activator expression, unlike that of urokinase, its receptor, and plasminogen activator inhibitor-1, is increased in chronic venous ulcers. Br J Dermatol, 2004 151(6): p. 1189-96

We claim:

1. A bifunctional peptide activating synthesis of collagen and inhibiting production of matrix metallo-proteinases, said peptide comprising:
   a sequence comprising a first peptide portion A, a second peptide portion B, and a third peptide portion C,
   wherein the first peptide portion A corresponds to a hexapeptide repeated at least three times, said first peptide portion A bonding to an elastin-binding receptor protein in order to stimulate collagen synthesis,
   wherein the second peptide portion B corresponds to a tetrapeptide acting as a competitive inhibitor of urokinase protease and being cleaved by said urokinase protease, and
   wherein the third peptide portion C corresponds to a tripeptide occupying at least one active site of the matrix metallo-proteinases in order to permit an inhibition of said proteinases.

2. The bifunctional peptide according to claim 1, wherein the first peptide portion A comprises:
   XGXXPG (SEQ ID NO: 28), being repeated at least three times, wherein a first X corresponds to any amino acid, wherein a second X corresponds to an amino acid selected from a group consisting of Val, Thr, Gln, Ala, and Leu, and wherein a third X corresponds to an amino acid selected from a group consisting of Ala, Leu, and Ile.

3. The bifunctional peptide according to claim 2, wherein the first peptide portion A of said peptide comprises VGVAPG (SEQ. ID NO: 29).

4. The bifunctional peptide according to claim 1, wherein the second peptide portion B, cleavable by a protease, comprises a RXRX (SEQ. ID NO: 30) with the first X and the second X being Y1 and Y2, respectively, wherein each of Y1 and Y2 correspond to an amino acid selected from a group consisting of Ser, Tyr, Gly, Ala, Arg, Val, and Leu.

5. The bifunctional peptide according to claim 4, wherein the second peptide portion B of said peptide comprises RVRL (SEQ. ID NO. 31).

6. The bifunctional peptide according to claim 1, wherein the third peptide portion C, permitting an inhibition of matrix metallo-proteinases, comprises Z1-Ile-Z2, wherein Z1 corresponds to an amino acid selected from a group consisting of Gly, Ile, and Leu, and wherein Z2 corresponds to an amino acid selected from a group consisting of Leu, Phe, Ala, Ile, and Val.

7. The bifunctional peptide according to claim 6, wherein the third peptide portion C of said peptide comprises Gly-Ile-Leu.

8. The bifunctional peptide according to claim 1, wherein said sequence is comprised of:
   VGVAPGVAVAPGVAVAPGRVRLGIL (SEQ. ID NO. 1), wherein N-terminal and C-terminal ends correspond to N and OH, respectively, and
   wherein VGVAPG (SEQ. ID NO: 29) repeats n times, and wherein n is 3.

9. The bifunctional peptide according to claim 1, further comprising one sequence selected from a group of sequences consisting of SEQ ID No. 2 to SEQ ID No. 26.

10. The bifunctional peptide according to claim 1, being obtained by chemical synthesis.

11. The bifunctional peptide according to claim 1, being preserved in lyophilized form.

12. The bifunctional peptide according to claim 1 for treatment of chronic scarring diseases.

13. The bifunctional peptide according to claim 12, for treatment of pressure sores or ulcers.

14. The bifunctional peptide according to claim 1, for the repair and/or regeneration of dermal tissue.

15. The bifunctional peptide according to claim 14 for treatment of skin aging.

16. A composition, comprising the bifunctional peptide according to claim 1.

17. The composition according to claim 16, wherein concentration of the bifunctional peptide varies between 10 µg/mL and 1 mg/mL.

* * * * *

SEQUENCE LISTING

<160> NUMBER OF SEQ ID NOS: 32

<210> SEQ ID NO 1
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 1

Val Gly Val Ala Pro Gly Val Gly Val Ala Pro Gly Val
1               5                   10

Gly Val Ala Pro Gly Arg Val Arg Leu Gly Ile Leu
        15                  20                  25

<210> SEQ ID NO 2
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 2

Val Gly Thr Ala Pro Gly Val Gly Thr Ala Pro Gly Val
1               5                   10

Gly Thr Ala Pro Gly Arg Val Arg Leu Gly Ile Leu
        15                  20                  25

<210> SEQ ID NO 3
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 3

Val Gly Gln Ala Pro Gly Val Gly Gln Ala Pro Gly Val
1               5                   10

Gly Gln Ala Pro Gly Arg Val Arg Leu Gly Ile Leu
        15                  20                  25

<210> SEQ ID NO 4
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 4

Val Gly Ala Ala Pro Gly Val Gly Ala Ala Pro Gly Val
1               5                   10

Gly Ala Ala Pro Gly Arg Val Arg Leu Gly Ile Leu
        15                  20                  25

<210> SEQ ID NO 5
<211> LENGTH: 25
<212> TYPE: PRT
<213> ORGANISM: Artificial sequence

```
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 5

Val Gly Leu Ala Pro Gly Val Gly Leu Ala Pro Gly Val
1               5                   10

Gly Leu Ala Pro Gly Arg Val Arg Leu Gly Ile Leu
        15                  20                  25

<210> SEQ ID NO 6
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 6

Val Gly Val Leu Pro Gly Val Gly Val Leu Pro Gly Val
1               5                   10

Gly Val Leu Pro Gly Arg Val Arg Leu Gly Ile Leu
        15                  20                  25

<210> SEQ ID NO 7
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 7

Val Gly Val Ile Pro Gly Val Gly Val Ile Pro Gly Val
1               5                   10

Gly Val Ile Pro Gly Arg Val Arg Leu Gly Ile Leu
        15                  20                  25

<210> SEQ ID NO 8
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 8

Val Gly Val Ala Pro Gly Val Gly Val Ala Pro Gly Val
1               5                   10

Gly Val Ala Pro Gly Arg Val Arg Leu Ile Ile Leu
        15                  20                  25

<210> SEQ ID NO 9
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 9
```

```
Val Gly Val Ala Pro Gly Val Gly Val Ala Pro Gly Val
1               5                   10

Gly Val Ala Pro Gly Arg Val Arg Leu Leu Ile Leu
        15                  20              25

<210> SEQ ID NO 10
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 10

Val Gly Val Ala Pro Gly Val Gly Val Ala Pro Gly Val
1               5                   10

Gly Val Ala Pro Gly Arg Val Arg Leu Gly Val Leu
        15                  20              25

<210> SEQ ID NO 11
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 11

Val Gly Val Ala Pro Gly Val Gly Val Ala Pro Gly Val
1               5                   10

Gly Val Ala Pro Gly Arg Val Arg Leu Gly Ala Leu
        15                  20              25

<210> SEQ ID NO 12
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 12

Val Gly Val Ala Pro Gly Val Gly Val Ala Pro Gly Val
1               5                   10

Gly Val Ala Pro Gly Arg Val Arg Leu Gly Gly Leu
        15                  20              25

<210> SEQ ID NO 13
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 13

Val Gly Val Ala Pro Gly Val Gly Val Ala Pro Gly Val
1               5                   10

Gly Val Ala Pro Gly Arg Val Arg Leu Gly Ile Phe
        15                  20              25
```

-continued

```
<210> SEQ ID NO 14
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 14

Val Gly Val Ala Pro Gly Val Gly Val Ala Pro Gly Val
1               5                   10

Gly Val Ala Pro Gly Arg Val Arg Leu Gly Ile Ala
    15                  20                  25

<210> SEQ ID NO 15
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 15

Val Gly Val Ala Pro Gly Val Gly Val Ala Pro Gly Val
1               5                   10

Gly Val Ala Pro Gly Arg Val Arg Leu Gly Ile Ile
    15                  20                  25

<210> SEQ ID NO 16
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 16

Val Gly Val Ala Pro Gly Val Gly Val Ala Pro Gly Val
1               5                   10

Gly Val Ala Pro Gly Arg Val Arg Leu Gly Ile Val
    15                  20                  25

<210> SEQ ID NO 17
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 17

Val Gly Val Ala Pro Gly Val Gly Val Ala Pro Gly Val
1               5                   10

Gly Val Ala Pro Gly Arg Ser Arg Leu Gly Ile Leu
    15                  20                  25

<210> SEQ ID NO 18
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
``` of matrix metallo-proteinases

<400> SEQUENCE: 18

Val Gly Val Ala Pro Gly Val Gly Val Ala Pro Gly Val
1               5                   10

Gly Val Ala Pro Gly Arg Tyr Arg Leu Gly Ile Leu
        15                  20                  25

<210> SEQ ID NO 19
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 19

Val Gly Val Ala Pro Gly Val Gly Val Ala Pro Gly Val
1               5                   10

Gly Val Ala Pro Gly Arg Gly Arg Leu Gly Ile Leu
        15                  20                  25

<210> SEQ ID NO 20
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 20

Val Gly Val Ala Pro Gly Val Gly Val Ala Pro Gly Val
1               5                   10

Gly Val Ala Pro Gly Arg Ala Arg Leu Gly Ile Leu
        15                  20                  25

<210> SEQ ID NO 21
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 21

Val Gly Val Ala Pro Gly Val Gly Val Ala Pro Gly Val
1               5                   10

Gly Val Ala Pro Gly Arg Arg Arg Leu Gly Ile Leu
        15                  20                  25

<210> SEQ ID NO 22
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 22

Val Gly Val Ala Pro Gly Val Gly Val Ala Pro Gly Val
1               5                   10

```
Gly Val Ala Pro Gly Arg Val Arg Ser Gly Ile Leu
        15                  20                  25
```

<210> SEQ ID NO 23
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 23

```
Val Gly Val Ala Pro Gly Val Gly Val Ala Pro Gly Val
1               5                   10

Gly Val Ala Pro Gly Arg Val Arg Tyr Gly Ile Leu
        15                  20                  25
```

<210> SEQ ID NO 24
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 24

```
Val Gly Val Ala Pro Gly Val Gly Val Ala Pro Gly Val
1               5                   10

Gly Val Ala Pro Gly Arg Val Arg Gly Gly Ile Leu
        15                  20                  25
```

<210> SEQ ID NO 25
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 25

```
Val Gly Val Ala Pro Gly Val Gly Val Ala Pro Gly Val
1               5                   10

Gly Val Ala Pro Gly Arg Val Arg Ala Gly Ile Leu
        15                  20                  25
```

<210> SEQ ID NO 26
<211> LENGTH: 25
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 26

```
Val Gly Val Ala Pro Gly Val Gly Val Ala Pro Gly Val
1               5                   10

Gly Val Ala Pro Gly Arg Val Arg Arg Gly Ile Leu
        15                  20                  25
```

<210> SEQ ID NO 27
<211> LENGTH: 9
<212> TYPE: PRT

```
<213> ORGANISM: Artificial sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa indicates any amino acid
<220> FEATURE:
<221> NAME/KEY: misc_feature
<222> LOCATION: (2)..(2)
<223> OTHER INFORMATION: Xaa indicates any amino acid
<220> FEATURE:
<221> NAME/KEY: misc_feature
<222> LOCATION: (9)..(9)
<223> OTHER INFORMATION: Xaa indicates any amino acid

<400> SEQUENCE: 27

Xaa Xaa Val Gly Val Ala Pro Gly Xaa
1               5

<210> SEQ ID NO 28
<211> LENGTH: 6
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases
<220> FEATURE:
<221> NAME/KEY: misc_feature
<222> LOCATION: (1)..(1)
<223> OTHER INFORMATION: Xaa indicates any amino acid
<220> FEATURE:
<221> NAME/KEY: misc_feature
<222> LOCATION: (3)..(3)
<223> OTHER INFORMATION: Xaa indicates Val, Thr, Gln, Ala, or Leu
<220> FEATURE:
<221> NAME/KEY: misc_feature
<222> LOCATION: (4)..(4)
<223> OTHER INFORMATION: Xaa indicates Ala, Leu, or Ile

<400> SEQUENCE: 28

Xaa Gly Xaa Xaa Pro Gly
1               5

<210> SEQ ID NO 29
<211> LENGTH: 6
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 29

Val Gly Val Ala Pro Gly
1               5

<210> SEQ ID NO 30
<211> LENGTH: 4
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases
<220> FEATURE:
<221> NAME/KEY: misc_feature
<222> LOCATION: (2)..(2)
<223> OTHER INFORMATION: Xaa indicates Ser, Tyr, Gly, Ala, Arg, Val, or
      Leu
<220> FEATURE:
<221> NAME/KEY: misc_feature
```

```
<222> LOCATION: (4)..(4)
<223> OTHER INFORMATION: Xaa indicates Ser, Tyr, Gly, Ala, Arg, Val, or
      Leu

<400> SEQUENCE: 30

Arg Xaa Arg Xaa
1

<210> SEQ ID NO 31
<211> LENGTH: 4
<212> TYPE: PRT
<213> ORGANISM: Artificial sequence
<220> FEATURE:
<223> OTHER INFORMATION: Synthesized Bifunctional Peptide capable of
      activating the collagen synthesis and inhibiting the production
      of matrix metallo-proteinases

<400> SEQUENCE: 31

Arg Val Arg Leu
1

<210> SEQ ID NO 32
<211> LENGTH: 6
<212> TYPE: PRT
<213> ORGANISM: Artificial sequence
<220> FEATURE:
<223> OTHER INFORMATION: synthetic peptide

<400> SEQUENCE: 32

Arg Val Arg Leu Ile Leu
1               5
```